(12) United States Patent
Machhammer et al.

(10) Patent No.: US 8,853,478 B2
(45) Date of Patent: Oct. 7, 2014

(54) METHOD FOR THE INTEGRATED PRODUCTION OF CELLULOSE AND LOW-MOLECULAR-WEIGHT REUSABLE MATERIALS

(75) Inventors: Otto Machhammer, Mannheim (DE); Jochem Henkelmann, Mannheim (DE); Wolfgang Rohde, Speyer (DE); Mario Emmeluth, Bensheim (DE); Sonja Giesa, Darmstadt (DE)

(73) Assignee: BASF SE, Ludwigshafen (DE)

( * ) Notice: Subject to any disclaimer, the term of this patent is extended or adjusted under 35 U.S.C. 154(b) by 485 days.

(21) Appl. No.: 13/062,732

(22) PCT Filed: Sep. 7, 2009

(86) PCT No.: PCT/EP2009/061529
§ 371 (c)(1),
(2), (4) Date: Jun. 6, 2011

(87) PCT Pub. No.: WO2010/026244
PCT Pub. Date: Mar. 11, 2010

(65) Prior Publication Data
US 2011/0268652 A1    Nov. 3, 2011

(30) Foreign Application Priority Data

Sep. 8, 2008    (EP) ................... 08163886

(51) Int. Cl.
| | |
|---|---|
| C07C 1/00 | (2006.01) |
| D21C 9/12 | (2006.01) |
| C07C 41/18 | (2006.01) |
| C07C 37/54 | (2006.01) |
| D21C 11/00 | (2006.01) |

(52) U.S. Cl.
CPC ............... *C07C 37/54* (2013.01); *C07C 41/18* (2013.01); *D21C 11/0007* (2013.01)

USPC ............... 585/242; 162/71; 162/82; 162/91; 162/173; 162/176; 162/189

(58) Field of Classification Search
USPC ......... 585/242; 162/71, 82, 91, 173, 176, 189
See application file for complete search history.

(56) References Cited

U.S. PATENT DOCUMENTS

| | | | |
|---|---|---|---|
| 2,057,117 A | 10/1936 | Sandborn et al. | |
| 2,104,701 A | 1/1938 | Sandborn et al. | |

(Continued)

FOREIGN PATENT DOCUMENTS

| | | |
|---|---|---|
| DE | 1 009 472 | 5/1957 |
| DE | 1 926 673 | 12/1969 |

(Continued)

OTHER PUBLICATIONS

Smook, Handbook for Pulp and Paper Technologists, 1992, Angus Wilde Publications, 2nd edition, chapter 10.*

(Continued)

*Primary Examiner* — Nina Bhat
(74) *Attorney, Agent, or Firm* — Oblon, Spivak, McClelland, Maier & Neustadt, L.L.P.

(57) ABSTRACT

The present invention relates to an integrated method for producing cellulose and at least one low-molecular-weight reusable material, in which a starting material containing lignocellulose is provided and subjected to a decomposition with a processing medium. A fraction enriched with cellulose and a fraction depleted of cellulose is then isolated from the decomposition material, the depleted fraction of cellulose being subjected to a treatment during which at least one low-molecular-weight reusable material is obtained.

35 Claims, 3 Drawing Sheets

(56) References Cited

U.S. PATENT DOCUMENTS

Figure 1:
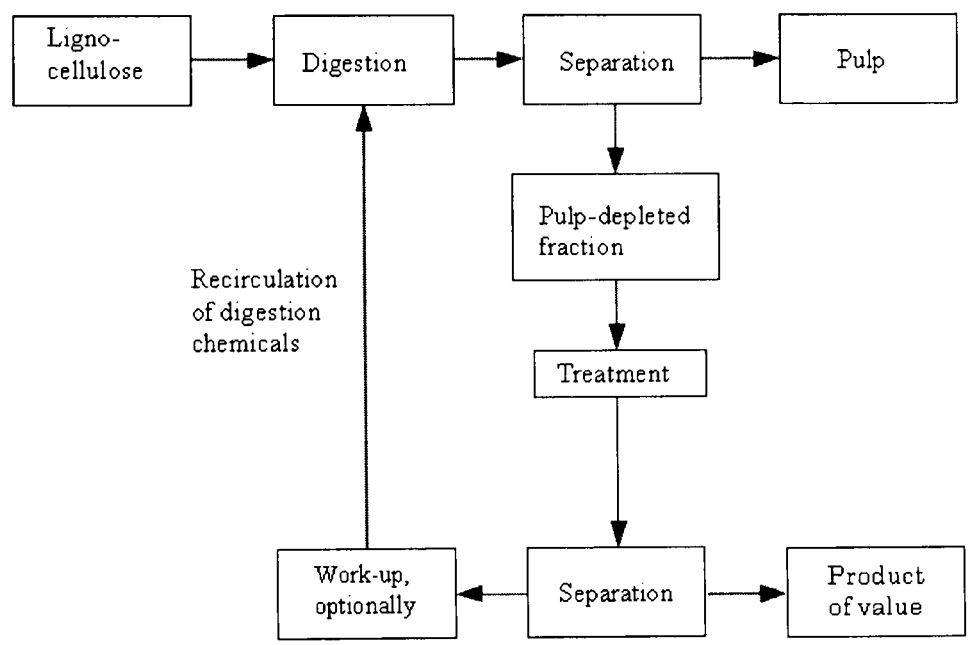

| | | | |
|---|---|---|---|
| 2,296,952 | A | 9/1942 | Ross et al. |
| 3,054,659 | A | 9/1963 | Craig et al. |
| 3,375,283 | A | 3/1968 | Goheen et al. |
| 3,577,467 | A | 5/1971 | Goldstein et al. |
| 4,259,151 | A * | 3/1981 | Gordy .......................... 162/239 |
| 4,900,873 | A | 2/1990 | Kakemoto et al. |
| 5,482,118 | A * | 1/1996 | Clough .......................... 166/279 |
| 5,959,167 | A * | 9/1999 | Shabtai et al. ................. 585/242 |
| 6,172,272 | B1 | 1/2001 | Shabtai et al. |
| 6,183,597 | B1 | 2/2001 | Siegle |
| 7,402,224 | B1 * | 7/2008 | Avignon et al. ................. 162/76 |
| 2002/0129910 | A1 * | 9/2002 | Lightner ........................ 162/16 |
| 2009/0218061 | A1 | 9/2009 | Schinski et al. |
| 2009/0218062 | A1 * | 9/2009 | Schinski et al. .............. 162/189 |
| 2010/0240934 | A1 | 9/2010 | Henkelmann et al. |
| 2010/0312023 | A1 | 12/2010 | Henkelmann et al. |
| 2010/0312024 | A1 | 12/2010 | Henkelmann et al. |
| 2010/0317889 | A1 | 12/2010 | Boehling et al. |
| 2011/0089046 | A1 | 4/2011 | Griesbach et al. |

FOREIGN PATENT DOCUMENTS

| | | |
|---|---|---|
| DE | 195 16 151 | 11/1996 |
| GB | 691 911 | 5/1953 |
| WO | 87 01695 | 3/1987 |
| WO | WO 04/106624 | * 12/2003 |
| WO | 2006 031175 | 3/2006 |
| WO | 2006 119357 | 11/2006 |
| WO | 2009 108599 | 9/2009 |
| WO | 2009 108601 | 9/2009 |

OTHER PUBLICATIONS

U.S. Appl. No. 13/100,394, filed May 4, 2011, Prochazka, et al.
U.S. Appl. No. 13/101,368, filed May 5, 2011, Prochazka, et al.
U.S. Appl. No. 13/101,374, filed May 5, 2011, Prochazka, et al.
Ira T. Clark, et al., "Production of Phenols by Cooking Kraft Lignin in Alkaline Solutions", Tappi, vol. 51, No. 1, Jan. 1968, pp. 44-48.
Terje Enkvist, et al., "The Demethylation and Degradation of Lignin or Spent Liquors by Heating with Alkaline Reagents*", Tappi, vol. 45, No. 2, Feb. 1962, pp. 128-135.
International Search Report Issued Jan. 29, 2010 in PCT/EP09/061529 filed Sep. 7, 2009.

* cited by examiner

METHOD FOR THE INTEGRATED PRODUCTION OF CELLULOSE AND LOW-MOLECULAR-WEIGHT REUSABLE MATERIALS

The present invention relates to an integrated process for producing pulp and at least one low molecular weight material of value, in which a lignocellulose-comprising starting material is provided and subjected to digestion with a treatment medium, a cellulose-enriched fraction and a cellulose-depleted fraction are isolated from the digested material and the cellulose-depleted fraction is subjected to a treatment to give at least one low molecular weight material of value.

Cellulose makes up an amount of about 700 billion metric tons of the estimated biomass stock of 1.5 trillion metric tons and is therefore the most important representative of the group of organic biopolymers and a raw material which is used in a wide variety of ways. However, cellulose rarely occurs in pure or sufficiently enriched form in the biomass available as raw material source but is mostly present as a constituent of lignocellulose. The digestion and the fractionation of lignocellulose into its main constituents, cellulose, lignin and optionally hemicellulose are central tasks of a biorefinery concept which is still to be created and is intended to make possible the effective and economical utilization of this renewable raw material.

The chemical digestion of lignocellulose results in a mass which comprises predominantly cellulose and is referred to as pulp. Pulp is the basis of the production of wood-free paper which does not undergo yellowing. The pulp for paper is produced predominantly from chipped wood (wood chips), but other plant fibers are also used.

There are two types of pulp processes, which dominate the market, the acid sulfite process (Mitscherlich process) and the alkaline sulfate process. Nowadays, mainly the sulfate process, also referred to as Kraft process, is used worldwide. It is named after the $Na_2SO_4$ added as "make-up chemical" in the recovery of the digestion chemicals; the actual active substances are sodium hydroxide and sodium sulfide. Alternatively, sulfur-free processes, e.g. the sodium carbonate digestion process, are also widespread. In this process, too, sodium hydroxide rather than sodium carbonate is generally used as base, with the latter serving only as make-up chemical in the recovery of the alkali. This group of digestion processes also includes alkali-oxygen digestion, alkali-peroxide digestion, etc. In all alkaline digestion processes, it has been found to be advantageous to add a small amount of anthraquinone (e.g. sodium carbonate-anthraquinone digestion). Here, the anthraquinone stabilizes the polysaccharides by suppressing their degradation from the end of the chain. Furthermore, there are many alternative digestion processes in which various treatment media capable of very selectively dissolving the substances which accompany the cellulose, especially the lignin, are used. Digestions using organic solvents are referred to as organosolv processes. Thus, for example, low-boiling alcohols (methanol, ethanol) are used in the alcell process. Boiling of a lignocellulose material in these alcohols enables lignin to be partially hydrolyzed and brought into solution. In this process, a major part of the hemicelluloses is dissolved, so that the pulps obtained generally also comprise significant proportions of lignin but only small amounts of hemicelluloses. Organosolv processes which lead to low-lignin pulps are frequently made up of two stages, with an organic digestion medium being used in a first stage and an aqueous alkaline digestion medium being used in a second stage, e.g. in the organocell process.

Since the lignin is generally not completely removed from the pulp in the abovementioned processes, the residual lignin can be removed in subsequent bleaching operations, e.g. by means of ozone or oxygen but only rarely using chlorine.

There continues to be a need for a process for producing pulp, in which the lignin comprising lignocellulose starting material is also passed to a high-value use. In terms of the material circuits for the process chemicals and solvents used, lignin recovery and further processing should be integrated as completely as possible into the process for pulp production.

WO 2006/031175 describes a process for isolating lignin from a black liquor, in which the latter is acidified and dewatered in order to precipitate the lignin.

U.S. Pat. No. 2,057,117 describes a process for preparing vanillin, in which a starting material selected from among lignocellulose, a crude lignin extract and lignosulfonic acid is heated with an aqueous alkali metal hydroxide solution under superatmospheric pressure and the reaction mixture obtained is admixed with sulfuric acid in order to precipitate organic constituents and convert the vanillin into a soluble form.

U.S. Pat. No. 2,104,701 describes a process for preparing vanillin, in which a starting material selected from among lignocellulose, a crude lignin extract and lignosulfonic acid is heated with an aqueous alkali metal hydroxide solution under superatmospheric pressure and the lignin is extracted from the resulting reaction mixture by means of a water-insoluble alcohol.

U.S. Pat. Nos. 5,959,167 and 6,172,272 describe processes for obtaining fuel from lignin, in which the latter is subjected to a base-catalyzed depolymerization in the presence of an alcohol in the supercritical state and hydroprocessing. The products obtained have a significant content of paraffins and saturated cyclic hydrocarbon compounds.

WO 2006/119357 describes a process for obtaining fuel from lignin, in which the latter is subjected to a base-catalyzed partial depolymerization and hydroprocessing to give a biofuel.

DE-OS-19 26 673 describes a process for hydrolyzing a lignin material to produce phenolic substances having a low molecular weight. The lignin material here originates from the alkaline digestion of lignocellulose. It is considered to be critical that the lignin is subjected to intermediate isolation and a base-free lignin material is used for the depolymerization.

U.S. Pat. No. 3,375,283 describes the preparation of methoxyphenols from wastewater from pulp production and specifically from a black liquor from the Kraft process. It is an essential feature of this process that the black liquor is firstly evaporated to dryness at a temperature below 150° C., i.e. below the depolymerization temperature. The dried residue is subsequently subjected to a pyrolysis at a temperature in the range from 300 to 600° C. with circulation of the material being pyrolyzed. The pyrolysis gases are subjected to a condensation to give a condensate enriched in methoxyphenols together with incondensable gases, i.e. CO, $CO_2$, $CH_3SH$ and $H_2S$. The gases can be burnt to generate heat or be used to produce methyl mercaptan. Isolation and recirculation of the digestion chemicals from pulp production with the aim of obtaining a closed materials circuit is not described.

In Tappi, vol. 45, No. 2, February 1962, pages 128-135, T. Enkvist, J. Turunen and T. Ashorn describe the demethylation and degradation of lignin or of liquors from the Kraft process by heating under pressure in the presence of basic reagents. To analyze the products obtained, the reaction mixtures are acidified and extracted with ether. This is a purely scientific study, without integration into a pulp process.

In Tappi, Vol. 51, No. 1, January 1968, pp. 44-48, I. T. Clark and J. Green describe the alkaline depolymerization of Kraft lignin in a solution of sodium hydroxide and sodium sulfide at a temperature of from 260 to 310° C. The aromatics obtained were examined as a function of the concentration of the sodium hydroxide, the presence or absence of sodium sulfide, the temperature and the reaction time. This is a scientific study on samples in the milliliter range using commercially procured Kraft lignin.

It has now surprisingly been found that the production of further materials of value, in particular an aromatics composition from lignin, can be advantageously integrated into the pulp process.

The invention therefore firstly provides an integrated process for producing pulp and at least one low molecular weight material of value, wherein
a) a lignocellulose-comprising starting material is provided and subjected to digestion with a treatment medium,
b) a cellulose-enriched fraction and at least one cellulose-depleted fraction are isolated from the digested material, with the cellulose-depleted fraction comprising at least part of the treatment medium from step a),
c) the cellulose-depleted fraction is subjected to a treatment to give at least one low molecular weight material of value and
d) the material/materials of value are isolated from the treatment product obtained in step c).

The term "low molecular weight materials of value" comprises, for the purposes of the invention, compounds other than pulp which have a molecular weight lower than the compounds comprising the lignocellulose-comprising starting material. These are, for example, selected from among hydrogen and unfunctionalized and functionalized aliphatic, cycloaliphatic and aromatic hydrocarbons. These include especially hydrogen, alkanes (e.g. methane, ethane, propane, butane, etc.), alkenes, alkadienes, alkanols (e.g. methanol, ethanol, etc.), aliphatic aldehydes (e.g. formaldehyde, acetaldehyde, etc.), cycloalkanes, cycloalkenes, cycloalkadienes, cycloalkanols, cycloalkadienols, cycloalkane polyols having more than 2 OH groups, aromatic hydrocarbons (such as benzene; alkylated benzenes, such as toluene and xylene; more highly condensed aromatic hydrocarbons and also monoalkylated, dialkylated and polyalkylated more highly condensed aromatics), aromatic alcohols (e.g. phenols; monoalkylated, dialkylated and polyalkylated phenols; more highly condensed aromatics having one, two or more than two OH groups; monoalkylated, dialkylated or more highly alkylated, more highly condensed aromatics having one, two or more than two OH groups; alkoxylated derivatives of the above-mentioned aromatic alcohols; etc.), aromatic aldehydes and mixtures thereof.

A specific embodiment of the invention is an integrated process for producing pulp and at least one low molecular weight material of value, wherein
a) a lignocellulose-comprising starting material is provided and subjected to digestion with a treatment medium,
b) a cellulose-enriched fraction and at least one cellulose-depleted fraction are isolated from the digested material, with the cellulose-depleted fraction comprising at least part of the treatment medium from step a),
c) the cellulose-depleted fraction is subjected to a treatment to give at least one low molecular weight material of value,
d) the material/materials of value is/are isolated from the treatment product obtained in step c),
e) the material(s) of value isolated in step d) is/are optionally subjected to a fractionation and/or at least one subsequent reaction,
f) a residue is isolated in step d) from the treatment product and subjected to a further treatment to give at least one component which is comprised in the treatment medium used in step a) and
g) the component(s) of the treatment medium obtained in step f) is/are recirculated to step a).

A more specific embodiment of the invention is an integrated process for producing pulp and an aromatics composition, wherein
a) a lignocellulose-comprising starting material is provided and subjected to digestion with a treatment medium,
b) a cellulose-enriched fraction and a lignin-enriched fraction are isolated from the digested material, with the lignin-enriched fraction comprising at least part of the treatment medium from step a),
c) the lignin-enriched fraction is subjected to depolymerization and
d) an aromatics composition is isolated from the depolymerization product obtained in step c).

An even more specific embodiment is an integrated process for producing pulp and an aromatics composition, wherein
a) a lignocellulose-comprising starting material is provided and subjected to digestion with a treatment medium,
b) a cellulose-enriched fraction and a lignin-enriched fraction are isolated from the digested material, with the lignin-enriched fraction comprising at least part of the treatment medium from step a),
c) the lignin-enriched fraction is subjected to depolymerization,
d) an aromatics composition is isolated by extraction from the depolymerization product obtained in step c),
e) the aromatics composition isolated in step d) is optionally subjected to a fractionation and/or at least one subsequent reaction,
f) an aromatics-depleted residue is isolated in step d) from the depolymerization product and subjected to further processing to give at least one component which is comprised in the treatment medium used in step a), and
g) the component(s) of the treatment medium obtained in step f) is/are recirculated to step a).

The process of the invention is distinguished by at least one of the following aspects:
  The process for obtaining at least one material of value (especially an aromatics composition from lignin) is integrated into a process for obtaining pulp.
  It is generally not necessary to isolate the components used for the treatment in step c) as intermediate. In particular, it is not necessary to isolate the lignin as intermediate in order to produce an aromatics composition.
  In general, the treatment for obtaining at least one material of value can be carried out in the treatment medium used for digestion of the lignocellulose-comprising starting material. In particular, the depolymerization to obtain the aromatics composition is carried out in the treatment medium used for digestion of the lignocellulose-comprising starting material. Here, the treatment medium used for obtaining the aromatics composition can comprise a liquid component and also at least part of the components used in the digestion of the lignocellulose-comprising starting material (process chemicals) or products derived therefrom.
  The treatment medium used for digestion of the lignocellulose-comprising starting material can be recirculated after the materials of value have been separated off.
  The supplementation and/or work-up of the components of the treatment medium (process chemicals) consumed in the digestion of the lignocellulose-comprising starting material and/or in the production of the materials of value can be carried out in the existing stages of the process for the production of pulp.

Overall, there is the opportunity to form product circuits which are closed in respect of the digestion chemicals, treatment media and washing media used.

The process integration enables concomitant use to be made of the process steps of pulp production, i.e. fewer process steps are necessary for producing materials of value and especially aromatics from lignin than in the case of the prior art.

In the pulp process, the facility for burning the evaporated black liquor is the most expensive plant component. In existing conventional plants, it is not really feasible to increase the production capacity because the heat-exchange area present for heat recovery is virtually impossible to increase. The reduction in the organic burden in the washing liquor as a result of the integrated production of material of value according to the process of the invention leads to an advantageous decrease in the load on heat recovery. If process chemicals comprised in the washing liquor right from the digestion of the lignocellulose starting material are additionally consumed in the production of material of value according to the process of the invention, there is an additional reduction in load since more heat is consumed for the reduction of the process chemicals which likewise takes place in the incineration plant and less heat therefore has to be removed via the heat-exchange areas. Both lead to the production capacity of an existing pulp plant being able to be increased relatively inexpensively by means of the integrated process of the invention.

In addition, the transport requirement can be reduced in the integrated process of the invention. For example, when the intermediate isolation of lignin is dispensed with, it is the high-value process product (aromatics) obtained rather than low-value lignin pellets or washing liquor which have significantly higher specific volumes and weights based on the product of value (e.g. phenol), which have to be transported. In addition, in the case of, for example, the external utilization of washing liquor, it is not necessary to transport any recycled streams in order to recirculate the process chemicals.

Lignocellulose forms the structural framework of the cell wall of plants and comprises cellulose, lignin and hemicelluloses as main constituents. Further constituents are, for example, silicates, ash (minerals), extractable low molecular weight organic compounds (known as extractables, e.g. terpenes, resins, fats), polymers, such as proteins, nucleic acids and vegetable gum (known as exsudate), etc.

Cellulose is a generally highly crystalline biopolymer of D-anhydroglucopyranose having long chains of sugar units linked by β-1,4-glycosidic bonds. The individual polymer chains are connected to one another by intermolecular and intramolecular hydrogen bonds and van der Waals interactions.

Lignin is a high molecular weight derivative of phenylpropane and has, depending on the natural source, one or more methoxy groups on the phenyl rings and at least one hydroxy group on the propyl units. Typical structural units of lignin are p-hydroxyphenylpropane, guaiacylpropane and syringylpropane, which are joined to one another by ether bonds and carbon-carbon bonds.

Step a)

In step a) of the process of the invention, a lignocellulose-comprising starting material (lignocellulose material) is provided and subjected to digestion. The digestion is intended to effect at least partial separation of the lignocellulose-comprising starting material into cellulose and substances accompanying cellulose. The substances accompanying cellulose include not only lignin but also hemicelluloses, silicates, ash (minerals), extractable low molecular weight organic compounds (known as extractables, e.g. terpenes, resins, fats), polymers (proteins, nucleic acids), vegetable gum (known as exudate), etc.

Lignocellulose-comprising starting materials suitable for use in step a) can, for example, be obtained from wood and plant fibers as starting material. Suitable lignocellulose materials are the various types of wood, i.e. broad-leaved timbers such as maple, birch, pear, oak, elm, ash, eucalyptus, beech, cherry, lime, nut, poplar, willow, etc. and conifers such as Douglas fir, spruce, yew, hemlock, pine, larch, fir, cedar, etc. Further suitable lignocellulose materials are cellulose-rich natural fibers such as flax, hemp, sisal, jute, straw, coconut fibers, switchgrass (*Panicum virgatum*) and other natural fibers. Suitable lignocellulose materials are also obtained, for example, as residue in the wood-processing industry. These include not only wood scrap but also sawdust, parquetry grinding dust, etc. Suitable lignocellulose materials are also obtained as residue in agriculture, e.g. in the harvesting of cereals (wheat straw, maize straw, etc), maize, sugar cane (bagasse), etc. Suitable lignocellulose materials are also obtained as residue in forestry, e.g. in the form of branches, bark, wood chips, etc. Another good source of lignocellulose materials is short rotation crops which make a high biomass production on a relatively small area possible.

The woody cell wall of central European timbers usually has approximately the following composition:

Broadleaved trees: cellulose 42-49%, hemicellulose 24-30%, lignin 25-30%, extractables 2-9%, ash (minerals) 0.2-0.8%.

Conifers: cellulose 42-51%, hemicellulose 27-40%, lignin 18-24%, extractables 1-10%, ash 0.2-0.8%.

It can be advantageous to subject the lignocellulose-comprising starting material to at least one pretreatment step before digestion. Such steps include, for example, mechanical comminution of the cellulose-comprising starting material, e.g. by shredding (chipping) and/or milling. Owing to their materials properties, fiber-comprising materials are preferably not subjected to pressure-shear comminution but to impact comminution. Suitable milling apparatuses are hammer mills, milling apparatuses operating according to the principle of jet milling and beater mills. The latter are especially suitable for high throughputs.

The process of the invention makes it possible to integrate the production of a composition of value (e.g. an aromatics composition) into a process for producing pulp. The integration can advantageously be effected into virtually all basic digestion processes.

Suitable processes for producing pulp can in principle be distinguished by at least one of the following features:

the treatment medium used in step a), the treatment conditions used in step a), the components used in a further process step, the process conditions used in a further process step.

The treatment medium used in step a) is capable of solubilizing at least part of the substances accompanying cellulose in the lignocellulose-comprising starting material under the digestion conditions described in more detail below. Here, in particular, at least partial, preferably essentially complete, solubilization of the lignin comprised in the lignocellulose-comprising starting material occurs. This means that preferably at least 50% by weight, particularly preferably at least 75% by weight, of the lignin comprised in the lignocellulose-comprising starting material is solubilized. The cellulose comprised in the lignocellulose-comprising starting material is not solubilized or solubilized only to a small extent in the treatment medium. This means that preferably not more than 20% by weight, particularly preferably not more than 10% by weight, of the cellulose comprised in the lignocellulose-comprising starting material is solubilized.

For the purposes of the invention, the term "solubilization" refers to conversion into a liquid state and comprises the production of solutions of the substances accompanying cellulose (especially of solutions of lignin), and also conversion into a solubilized state different therefrom. When a lignocellulose constituent is converted into a solubilized state, the individual molecules, e.g. polymer molecules, do not necessarily have to be surrounded completely by a solvation shell. The important thing is that the lignocellulose constituent goes over into a liquid state as a result of the solubilization. Solubilizates for the purposes of the invention therefore also include colloidal solutions, microdispersions, gels, etc.

The treatment medium used in step a) comprises at least one compound which is liquid under normal conditions (20° C. and 1.01325 bar). This is preferably selected from among water, acids, bases and organic solvents which are capable of at least partly solubilizing lignin without solubilizing relatively large amounts of cellulose. Mixtures of these liquid compounds are also suitable. In general, mixtures of acids and base are not used, but instead the corresponding salt is used in combination with at least one liquid compound. Acids and bases which are liquid under normal conditions can be selected by a person skilled in the art from among those described below. The organic solvents are preferably selected from among alcohols, such as methanol, ethanol, n-propanol, isopropanol, n-butanol, tert-butanol or phenol, diols and polyols, such as ethanediol and propanediol, amino alcohols, such as ethanolamine, diethanolamine or triethanolamine, aromatic hydrocarbons, such as benzene, toluene, ethylbenzene or xylenes, halogenated solvents, such as dichloromethane, chloroform, carbon tetrachloride, dichloroethane or chlorobenzene, aliphatic solvents, such as pentane, hexane, heptane, octane, ligroin, petroleum ether, cyclohexane or decalin, ethers, such as tetrahydrofuran, diethyl ether, methyl tert-butyl ether or diethylene glycol monomethyl ether, ketones, such as acetone or methyl ethyl ketone, esters, such as ethyl acetate, formamide, dimethylformamide (DMF), dimethylacetamide, dimethyl sulfoxide (DMSO), acetonitrile and mixtures thereof.

The liquid compound is preferably selected from among water, water-miscible organic solvents and mixtures thereof. The liquid compound is particularly preferably selected from among water, alcohols and mixtures thereof. Thus, it is possible to use water, methanol, ethanol, a mixture of water with methanol and/or ethanol, or a mixture of methanol and ethanol as liquid compound.

The treatment medium used in step a) can comprise at least one base. Suitable bases are alkali metal and alkaline earth metal hydroxides, e.g. sodium hydroxide, potassium hydroxide, calcium hydroxide or magnesium hydroxide, alkali metal and alkaline earth metal hydrogencarbonates, e.g. sodium hydrogencarbonate, potassium hydrogencarbonate, calcium hydrogencarbonate or magnesium hydrogencarbonate, alkali metal and alkaline earth metal carbonates, e.g. sodium carbonate, potassium carbonate, calcium carbonate or magnesium carbonate, alkaline earth metal oxides such as calcium oxide or magnesium oxide, and mixtures thereof.

The treatment medium used in step a) can comprise at least one acid. Brönsted acids or Lewis acids are suitable in principle. Suitable Brönsted acids are inorganic acids, their acidic salts and anhydrides. These include, for example, mineral acids, such as hydrochloric acid, nitric acid, sulfuric acid, phosphoric acid or amidosulfonic acid, but also ammonium salts, such as ammonium fluoride, ammonium chloride, ammonium bromide or ammonium sulfate. Further suitable acids are hydrogensulfates, such as sodium hydrogensulfate, potassium hydrogensulfate, calcium hydrogensulfate or magnesium hydrogensulfate. Further suitable acids are hydrogensulfites, such as sodium hydrogensulfite, potassium hydrogensulfite, calcium hydrogensulfite or magnesium hydrogensulfite. Further suitable acids are hydrogenphosphates and dihydrogenphosphates, e.g. sodium hydrogenphosphate, sodium dihydrogen-phosphate, potassium hydrogenphosphate or potassium dihydrogenphosphate. $SO_2$, $SO_3$ and $CO_2$ are also suitable.

Suitable Brönsted acids also include organic acids and their anhydrides, e.g. formic acid, acetic acid, methanesulfonic acid, trifluoroacetic acid or p-toluenesulfonic acid.

Suitable Lewis acids are all metal halides or semimetal halides, in which the metal or semimetal has an electron pair vacancy. Examples are $BF_3$, $BCl_3$, $BBr_3$, $AlF_3$, $AlCl_3$, $AlBr_3$, ethylaluminum dichloride, diethylaluminum chloride, $TiF_4$, $TiCl_4$, $TiBr_4$, $VCl_5$, $FeF_3$, $FeCl_3$, $FeBr_3$, $ZnF_2$, $ZnCl_2$, $ZnBr_2$, $Cu(I)F$, $Cu(I)Cl$, $Cu(I)Br$, $Cu(II)F_2$, $Cu(II)Cl_2$, $Cu(II)Br_2$, $Sb(III)F_3$, $Sb(V)F_5$, $Sb(III)Cl_3$, $Sb(V)Cl_5$, $Nb(V)Cl_5$, $Sn(II)F_2$, $Sn(II)Cl_2$, $Sn(II)Br_2$, $Sn(IV)F_4$, $Sn(IV)Cl_4$ and $Sn(IV)Br_4$.

The treatment medium used in step a) can comprise at least one salt different from the abovementioned compounds. The salts are preferably selected from among salts of the abovementioned acids and bases and their oxidation or reduction products. Suitable salts are, for example ammonium, alkali metal or alkaline earth metal sulfates, e.g. sodium sulfate, potassium sulfate, calcium sulfate or magnesium sulfate. Further suitable salts are ammonium, alkali metal or alkaline earth metal sulfites, e.g. sodium sulfite, potassium sulfite, calcium sulfite or magnesium sulfite. Further suitable salts are ammonium, alkali metal or alkaline earth metal sulfides, e.g. sodium sulfide, potassium sulfide, calcium sulfide or magnesium sulfide. Further suitable salts are alkali metal hydrogensulfides, such as sodium hydrogensulfide or potassium hydrogensulfide.

The treatment medium used in step a) can comprise further compounds different from the abovementioned compounds. Such compounds are especially the customary process chemicals known to those skilled in the art for the various digestion processes for the production of pulp from a lignocellulose-comprising starting material. The following details regarding individual embodiments of the digestion in step a) are incorporated by reference at this point.

The digestion in step a) can be carried out in one or more stages. In the simplest case, the digestion in step a) is carried out in a single stage. If the treatment is carried out in a plurality of stages, e.g. in 2, 3 or more than 3 stages, the individual stages can differ in respect of the treatment medium used and/or the treatment conditions. In a suitable embodiment of a two-stage digestion in step a), it is possible, for example to use at least one organic solvent or a mixture of water and at least one organic solvent in the first stage and to use an alkaline aqueous medium in the second stage. One such embodiment is, for example, the organocell process described in more detail below, in which the digestion in the first stage is carried out using a water/alcohol mixture and a digestion using aqueous NaOH is carried out in the second stage. In a further suitable embodiment of a two-stage digestion, it is possible, for example, for a subsequent stage to have a higher temperature and/or a higher pressure than the preceding stage. In a multistage digestion, the digested material from only one of the stages or from a plurality of stages can be used for further processing in step b). However, a condition is that a lignin-enriched fraction can be isolated from the digested material from the respective stage.

The digestion in step a) is preferably carried out at ambient temperature or preferably above ambient temperature. The temperature is preferably in the range from about 40 to 300° C., particularly preferably from 50 to 250° C. In a specific embodiment, the temperature is firstly increased stepwise or continuously during the course of the treatment until the desired final temperature has been reached.

The digestion in step a) can be carried out under reduced pressure, at ambient pressure or at above ambient pressure. The pressure in step a) is generally in the range from 0.01 bar to 300 bar, preferably from 0.1 bar to 100 bar.

The duration of the digestion in step a) is generally from 0.5 minutes to 7 days, preferably from 5 minutes to 96 hours.

Alkaline Treatment Medium

In a first preferred embodiment, an alkaline treatment medium is used in step a).

It can be advantageous to treat the lignocellulose-comprising starting material with mineral acid and/or steam before digestion with an alkaline treatment medium. Suitable mineral acids are, for example hydrochloric acid and in particular sulfuric acid. The treatment with steam is preferably carried out at a temperature in the range from about 110 to 300° C., particularly preferably from 120 to 250° C. Treatment of the lignocellulose-comprising starting material with mineral acid and/or steam before digestion with an alkaline treatment medium brings about at least a partial hydrolysis of the hemicelluloses comprised in the lignocellulose material. In the case of wood from conifers, generally from 10 to 15% by weight of the lignocellulose material, based on the total weight, goes into solution in the prehydrolysis. In the case of wood from broad-leaved trees, generally from 15 to 20% by weight of the lignocellulose material, based on the total weight, goes into solution in the prehydrolysis.

The digestion in step a) can then preferably be carried out by the sulfate process (Kraft process). The treatment medium used in step a) then comprises NaOH and $Na_2S$ as main components in an aqueous medium. In a specific embodiment, the treatment medium used in step a) comprises NaOH, $Na_2S$, $Na_2CO_3$ and $Na_2SO_4$ in an aqueous medium.

The digestion of the lignocellulose material with at least one alkaline treatment medium in step a) is preferably carried out at a temperature in the range from 50 to 300° C., particularly preferably from 70 to 250° C. In a specific embodiment, the temperature is firstly increased stepwise or continuously during the course of the treatment until the desired final temperature has been reached. For this purpose, the treatment can, for example, be carried out at a temperature in the range from about 50 to 130° C. in a first stage and in a range from about 130 to 250° C. in a second stage. The duration of the first stage is, for example, from 5 to 50% of the total treatment time. Heating is carried out using apparatuses customary for this purpose, e.g. by means of heat exchangers, heating baths, gas burners, etc. It is also possible to use heat obtained in other parts of the pulp process, e.g. from the combustion of organic constituents of the treatment medium after the aromatics composition has been separated off.

The pressure in the digestion of the lignocellulose material in step a) is generally in the range from 0.1 bar to 100 bar, preferably from 1 bar to 10 bar. In a specific embodiment, the digestion is carried out at ambient pressure.

The duration of the digestion of the lignocellulose material in step a) is generally from 0.5 minutes to 7 days, preferably from 5 minutes to 96 hours.

The digestion in step a) can also preferably be carried out by the soda process. The treatment medium used in step a) then comprises NaOH as main component in an aqueous medium which is essentially free of sulfur-comprising compounds. For the purposes of the present invention, an aqueous medium which is essentially free of sulfur-comprising compounds is a medium to which no sulfur-comprising compounds have been added as process chemicals. In this variant, the lignocellulose starting material used in step a) is preferably selected from among annual plants such as flax, hemp, sisal, jute, straw, coconut fibers, switchgrass (*Panicum virgatum*) and other short rotation crops.

The digestion of the lignocellulose material by the soda process in step a) is preferably carried out at a temperature in the range from 70 to 300° C., particularly preferably from 100 to 250° C.

The pressure in the digestion of the lignocellulose material in step a) according to the soda process is generally in the range from 0.1 bar to 100 bar, preferably 1 bar to 10 bar.

The duration of the digestion of the lignocellulose material in step a) according to the soda process is generally from 0.5 minutes to 7 days, preferably from 5 minutes to 96 hours.

The amount of NaOH used in the digestion of the lignocellulose material in step a) according to the soda process is generally in the range from 5 to 25 parts by weight, particularly preferably from 7 to 20 parts by weight, based on the total weight of the lignocellulose starting material used.

In a specific embodiment, an alkaline treatment medium is used in step a) and the digestion is carried out in an oxygen atmosphere. Such processes are likewise known and are referred to as alkali-oxygen digestion. The pressure in the digestion of the lignocellulose material in step a) is then generally in the range from 1.1 bar to 100 bar, preferably from 2 bar to 50 bar.

In a further specific embodiment, an alkaline treatment medium is used in step a) and the digestion is carried out in the presence of hydrogen peroxide and/or another peroxide compound. Such processes are likewise known and are also referred to as alkali-peroxide digestion.

In a further specific embodiment an alkaline treatment medium is used in step a) and the digestion is carried out in the presence of anthraquinone. The amount of anthraquinone used in the digestion of the lignocellulose material in step a) is generally in the range from 0.001 to 5 parts by weight, particularly preferably from 0.01 to 1 part by weight, based on the total weight of the lignocellulose starting material used.

Treatment Medium Comprising an Organic Solvent

In a second preferred embodiment, a treatment medium comprising at least one organic solvent is used in step a).

Digestion processes for lignocellulose using organic solvents are known in principle and are also referred to as organosolv processes.

Suitable organic solvents are those mentioned at the outset, which are incorporated by reference at this point. Preference is given to using an organic solvent selected from among $C_1$-$C_4$-alkanols, mixtures of $C_1$-$C_4$-alkanols and mixtures of at least one $C_1$-$C_4$-alkanol with water in step a). The $C_1$-$C_4$-alkanols are preferably selected form among methanol, ethanol, n-propanol, isopropanol and n-butanol. Preference is given to methanol, ethanol and mixtures thereof. Mixtures of at least one $C_1$-$C_4$-alkanol with water preferably comprise from 10 to 99% by weight, particularly preferably from 20 to 95% by weight, of at least one $C_1$-$C_4$-alkanol, based on the total weight of the mixture.

The digestion of the lignocellulose material with a treatment medium comprising at least one organic solvent in step a) is preferably carried out at a temperature in the range from 70 to 250° C., particularly preferably from 100 to 220° C.

The pressure in the digestion of the lignocellulose material with a treatment medium comprising at least one organic solvent in step a) is generally in the range from 1 bar to 100 bar, preferably from 2 bar to 50 bar.

In the digestion of the lignocellulose material with a treatment medium comprising at least one organic solvent in step a), an additional additive can be used to increase the selectivity of the solubilization of individual substances accompanying cellulose. Such additives include, for example, alkali metal hydroxides, such as sodium hydroxide; ammonium hydrogensulfite and also alkali metal and alkaline earth metal hydrogensulfites, such as sodium hydrogensulfite and magnesium hydrogensulfite. Further possible additives are mineral acids, such as hydrochloric acid, nitric acid, sulfuric acid, phosphoric acid or amidosulfonic acid and their ammonium, alkali metal and alkaline earth metal salts. Further suitable additives are organic acids, such as oxalic acid, formic acid or acetic acid. Peracids, such as persulfuric acid or peracetic acid are also suitable.

The following commercially employed organosolv processes are especially suitable for use in step a) of the process of the invention:

Alcell process: ethanol/water mixture as treatment medium. ASAM process: alkaline sulfite-anthraquinone-methanol treatment medium. Organocell process: two-stage process using an organic medium in the first stage and an alkaline medium in the second stage, e.g. digestion with methanol and/or ethanol in the first stage and with methanol and/or ethanol, NaOH, and optionally anthraquinone in the second stage.

Acetosolv process: acetic acid/hydrochloric acid mixture as treatment medium.

In a specific embodiment, the depolymerization in step a) is not carried out in the presence of an alcohol in the supercritical state.

Step b)

In step b) of the process of the invention, a cellulose-enriched fraction and at least one cellulose-depleted fraction are isolated from the digested material, with the cellulose-depleted fraction comprising at least part of the treatment medium from step a).

Preference is given to isolating at least one cellulose-depleted fraction comprising at least one component selected from among lignin, hemicellulose, cellulose, degradation products of the abovementioned components and mixtures thereof from the digested material.

In many cases, it is not critical in terms of the further treatment in step c) if a cellulose-depleted fraction which comprises a mixture of two or more than two different components is used. Alternatively, it is naturally possible to isolate a cellulose-depleted fraction or a plurality of cellulose-depleted fractions containing a main component from the digested material and then subjecting this to a further treatment in step c). For the present purposes, a main component is a component which makes up at least 20% by weight, preferably at least 50% by weight, in particular at least 75% by weight, of the cellulose-depleted fraction, based on the total weight of the fraction.

The isolation of the cellulose-enriched fraction and the cellulose-depleted fraction(s) in step b) is preferably carried out by filtration, centrifugation, extraction, precipitation, distillation, stripping or a combination thereof. A person skilled in the art can control the composition of the cellulose-depleted fraction(s) by means of the isolation process. The isolation can be carried out in one or more stages. It is thus possible, for example, to carry out a separation into the cellulose-enriched fraction and a first cellulose-depleted fraction in a first stage, e.g. by filtration and/or centrifugation. The first cellulose-depleted fraction can then be subjected to further fractionation in one or more further stages.

Customary filtration processes are, for example, cake and deep-bed filtration (e.g. as described in A. Rushton, A. S. Ward, R. G. Holdich: Solid-Liquid Filtration and Separation Technology, VCH Verlagsgesellschaft, Weinheim 1996, pages 177 ff., K. J. Ives, in A. Rushton (Hg.): Mathematical Models and Design Methods in Solid-Liquid Separation, NATO ASI series E No. 88, Martinus Nijhoff, Dordrecht 1985, pages 90 ff.) and Crossflow Filtrations (e.g. as described in J. Altmann, S. Ripperger, J. Membrane Sci. 124 (1997), pages 119-128). Customary centrifugation processes are described, for example, in G. Hultsch, H. Wilkesmann, "Filtering Centrifuges," in D. B. Purchas, Solid-Liquid Separation, Upland Press, Croydon 1977, pages 493-559; and in H. Trawinski, Die aquivalente Klärfläche von Zentrifugen, Chem. Ztg. 83 (1959), pages 606-612.

The extraction can be carried out using, for example, a solvent which is immiscible with the treatment medium used in step a) or at least one solvent having a miscibility gap in which the desired component (e.g. lignin) is sufficiently soluble. The extractant is for this purpose brought into intimate contact with the treatment medium and a phase separation is subsequently carried out. The extraction can be carried out in one or more stages by customary methods.

The removal of undecomposed volatile components can in principle be carried out by customary distillation processes known to those skilled in the art. Suitable apparatuses for the work-up by distillation are distillation columns, such as tray columns, which may be equipped with bubble caps, sieve plates, sieve trays, ordered packing, random packing elements, valves, side offtakes, etc., evaporators such as thin film evaporators, falling film evaporators, forced circulation evaporators, Sambay evaporators, etc., and combinations thereof. In a specific embodiment, the distillation is carried out using not the entire digested material from step a), but instead a fraction which has already been depleted in cellulose.

Suitable separation processes are described in the following documents: Sattler, Klaus: Thermische Trennverfahren, 3rd edition, Wiley VCH, 2001; Schlünder E. U., Thurner F.: Destillation, Absorption, Extraktion, Springer Verlag, 1995; Mersmann, Alfons: Thermische Verfahrenstechnik, Springer Verlag, 1980; Grassmann P., Widmer F.: Einführung in die thermische Verfahrenstechnik, de Gruyter, 1997; Weiß S., Militzer K.-E., Gramlich K.: Thermische Verfahrenstechnik, Dt. Verlag für Grundstoffindustrie, Leipzig, Stuttgart, 1993. These documents are hereby incorporated by reference.

In a specific embodiment, the isolation of a cellulose-enriched fraction and at least one cellulose-depleted fraction (=step b) and the subsequent treatment of the cellulose-depleted fraction to give a material of value (=step c), can be configured as a single stage, e.g. as a reactive distillation.

If step b) comprises at least one stripping process, this can be carried out in a customary manner, e.g. using $CO_2$ or steam as stripping gas.

As indicated above, the treatment medium used in step a) is capable of solubilizing at least part of the components comprised in the lignocellulose-comprising starting material, especially lignin. The cellulose comprised in the lignocellulose-comprising starting material is not solubilized or solubilized only to a small extent in the treatment medium. The isolation of the cellulose-enriched fraction and the (first) cellulose-depleted fraction is preferably carried out by filtration or centrifugation. To accelerate the filtration, it can be carried out with the pressure increased on the cellulose side or reduced on the outflow side.

The cellulose-enriched fraction isolated in step b) is preferably subjected to a purification to remove any remaining treatment medium from step a).

For this purpose, the cellulose-enriched fraction can be subjected to washing with a liquid washing medium. Suitable washing media are ones in which at least part of the components comprised in the treatment medium at the end of the digestion step a) readily dissolve and cellulose does not dissolve or dissolves only in small amounts. Preferred washing media are the liquid compounds described above as constituent of the treatment medium. The washing medium is particularly preferably selected from among water, water-miscible solvents and mixtures of water and at least one water-miscible solvent. Particular preference is given to using water as washing medium.

To carry out the purification, the cellulose-enriched fraction can be subjected once or a plurality of times in succession to a treatment with a washing medium. For this purpose, the cellulose is brought into intimate contact with the washing medium in a suitable apparatus and the washing medium is subsequently separated off from the cellulose. Suitable apparatuses are, for example, stirred vessels which, if required, can be provided with a heating facility and an apparatus for condensation and recirculation of the washing medium.

To achieve the desired aim of closed materials circuits, it is advantageous to use at least part of the washing medium together with the or one of the cellulose-depleted fraction(s) isolated in step b) for the further treatment in step c). For this reason, at least part of the washing medium is preferably combined with the cellulose-depleted fraction or, in the case of a plurality of such fractions, at least one cellulose-depleted fraction. In particular, the washing medium is all combined with the cellulose-depleted fraction(s).

In a first specific embodiment, a cellulose-enriched fraction and a hemicellulose-enriched fraction are isolated in step b) of the process of the invention from the digested material obtained in step a). Here, the hemicellulose-enriched fraction comprises at least part of the treatment medium from step a). The hemicellulose-enriched fraction is preferably subjected to treatment by hydrocracking, decarboxylation or a combination thereof in step c).

In a second specific embodiment, a cellulose-enriched fraction and a lignin-enriched fraction are isolated in step b) of the process of the invention from the digested material obtained in step a). Here, the lignin-enriched fraction comprises at least part of the treatment medium from step a). The lignin-enriched fraction is preferably subjected to treatment by depolymerization in step c).

As indicated above, the treatment medium used in step a) is capable of solubilizing at least part of the lignin comprised in the lignocellulose-comprising starting material. The isolation of the cellulose-enriched fraction and the lignin-enriched fraction in step b) is therefore preferably carried out by filtration or centrifugation. To accelerate the filtration, it can be carried out with the pressure increased on the cellulose side or reduced on the outflow side.

To achieve the desired aim of closed material circuits, it is also advantageous in the second specific embodiment to use at least part of the washing medium together with the lignin-enriched fraction isolated in step b) for the depolymerization in step c). For this reason, at least part of the washing medium is preferably combined with the lignin-enriched fraction. In particular, the washing medium is all combined with the lignin-enriched fraction.

In the following, the term "lignin-enriched fraction" also encompasses a fraction which further comprises a liquid washing medium from the washing of the cellulose-enriched fraction.

Step c)

In step c) at least one cellulose-depleted fraction is subjected to a treatment to give at least one material of value. The treatment in step c) is preferably selected from among depolymerization, hydrocracking, decarboxylation and combinations thereof.

As indicated above, it is not necessary in the process of the invention to isolate as intermediate the components used for the treatment in step c). The treatment in step c) is preferably carried out using a cellulose-depleted fraction which contains at least one compound which is liquid under standard conditions (20° C. and 1.01325 bar).

The cellulose-depleted fraction used for the treatment in step c) preferably has a proportion of compounds which are liquid under standard conditions of at least 10% by weight, particularly preferably at least 20% by weight, in particular at least 30% by weight.

The liquid compounds comprised in the cellulose-depleted fraction comprise at least one liquid compound from the treatment medium used in step a). The information about suitable and preferred liquid compounds in step a) is fully incorporated by reference at this point. The liquid compounds comprised in the cellulose-depleted fraction can additionally comprise at least one liquid compound from a washing medium obtained in the washing of the cellulose-enriched fraction. The information regarding suitable and preferred washing media in step b) is fully incorporated by reference at this point.

In a specific embodiment, the treatment of the cellulose-depleted fraction is carried out using a reactor whose surfaces which come into contact with the fraction comprise nickel or consist of nickel.

The cellulose-depleted fraction isolated in step b), which comprises at least part of the treatment medium from step a), can be subjected to a depolymerization in step c). According to the invention the depolymerization, is, in contrast to hydrocracking, not carried out with addition of hydrogen and/or hydrogen-comprising gases and/or hydrogen-donating compounds. For the purposes of the invention, depolymerization is the degradation of a polymeric starting material to give low molecular weight products. It includes, in particular, the degradation of a lignin starting material to give an aromatics composition. The depolymerization can, if desired, be carried out in the presence of at least one depolymerization catalyst. Suitable depolymerization catalysts are in principle all catalysts which are also used as catalysts for the formation of the polymers. They include, for example, silica, alumina, aluminosilicates, aluminosilicates having layer structures and zeolites, such as mordenite, faujasite, zeolite X, zeolite Y and ZSM-5, zirconium oxide and titanium dioxide.

The temperature in the depolymerization is preferably in the range from 100 to 350° C., particularly preferably from 150 to 300° C. If an alkaline, cellulose-depleted fraction which additionally comprises at least one sulfide and/or hydrogensulfide is used for the depolymerization in step c), the temperature is preferably in the range from 150 to 250° C. In a specific embodiment, a black liquor is subjected to a depolymerization at a temperature in the range from 150 to 250° C. The pressure in the depolymerization is preferably in the range from 1 to 250 bar, preferably from 1.1 to 40 bar. The residence time at the depolymerization temperature can range from a few seconds to a number of days. In a specific embodiment, the residence time at the depolymerization temperature is from 5 seconds to 5 minutes, especially from 10 seconds to 3 minutes.

The cellulose-depleted fraction isolated in step b), which comprises at least part of the treatment medium from step a) and also carbon-comprising biomass, can be subjected to hydrocracking in step c). For the present purposes, this is a treatment with hydrogen and/or hydrogen-comprising gases and/or hydrogen-donating compounds at elevated temperatures and, optionally, under superatmospheric pressure. The temperature in hydrocracking is preferably in the range from 50 to 1000° C., particularly preferably from 75 to 60° C. The pressure in hydrocracking is preferably in the range from 1 to 600 bar, preferably from 2 to 500 bar. Customary residence times are in the range from 1 minute to 24 hours, preferably from 15 minutes to 8 hours.

In general, this process makes it possible to process the cellulose-depleted fraction without further prior work-up to form hydrocarbon-comprising cracking gases. Depending on the starting material and cracking conditions, the cracking gas comprises alkanes, preferably $C_1$-$C_4$-alkanes, hydrocarbons boiling in the gasoline range and medium or heavy oils which can be used, for example, as diesel oil and for heating purposes.

Preference is given to using a hemicellulose-enriched fraction for hydrocracking. The process is also very well-suited for the joint hydrogenative treatment of cellulose-depleted fractions which have not been subjected to a separation into hemicellulose, lignin, etc. The hydrogenation of the cellulose-depleted fraction can be carried out very successfully without additional catalysts (i.e. without addition of further hydrogenation catalysts to the digestion chemicals comprised). However, to achieve better results in respect of conversion and selectivity to fractions having particular boiling ranges, the additional use of a catalyst can be advantageous. Suitable catalysts comprise, for example, Fe, Mo, Ni, Co, W and/or other hydrogenation-active metals and/or compounds and/or complexes thereof. The metals and/or their compounds and/or complexes can have been applied to supports, e.g. to aluminum oxide, silicon dioxide, aluminum silicates, zeolites and other supports or support mixtures known to those skilled in the art or else be used without supports. Particular zeolites are also themselves suitable as catalysts. As hydrogenation gas, it is possible to use various hydrogen grades. The presence of additional components such as CO, $CO_2$, $H_2S$, methane, ethane, water vapor, etc. can also be useful. Hydrogen grades as are obtained, for example, in gasification reactions of carbon-comprising materials by means of steam are very well-suited. Such materials can be residues from the processing of mineral oils, or coal, wood, peat or residues from the processing of coal, for example, hydrogenation. Biomass or vegetable material separated off from domestic waste is also suitable. Pure hydrogen is also very well-suited.

The cellulose-depleted fraction isolated in step b), which comprises at least part of the treatment medium from step a), can be subjected to a decarboxylation in step c). This is a formal elimination of $CO_2$. Decarboxylation processes are known to those skilled in the art.

In a preferred embodiment, a cellulose-depleted fraction, comprising at least part of the treatment medium from step a) is subjected to a depolymerization in step c) of the process of the invention. Particular preference is given to subjecting a lignin-enriched fraction to a depolymerization.

According to a specific embodiment described at the outset, the invention relates to an integrated process for producing pulp and an aromatics composition, wherein a) a lignocellulose-comprising starting material is provided and subjected to digestion with a treatment medium,
b) a cellulose-enriched fraction and a lignin-enriched fraction are isolated from the digested material, with the lignin-enriched fraction comprising at least part of the treatment medium from step a),
c) the lignin-enriched fraction is subjected to depolymerization and
d) an aromatics composition is isolated from the depolymerization product obtained in step c).

In a specific embodiment of the process of the invention, a black liquor from the digestion of a lignocellulose-comprising starting material with an alkaline treatment medium is used for the depolymerization in step c). In particular, a black liquor from sulfate digestion (Kraft digestion) is used for the depolymerization in step c).

If desired, part of the liquid compounds comprised in the lignin-enriched fraction can be removed from this fraction before the depolymerization in step c). Suitable apparatuses are the distillation apparatuses and evaporators, e.g. plate evaporators, rotary evaporators, falling film evaporators, forced circulation depressurization evaporators, short bath evaporators or thin film evaporators, customary for this purpose. The removal of the liquid compounds is then preferably carried out within a process for the production of pulp, into which the production of the aromatics composition is integrated. Thus, for example, a black liquor which has been taken off before or during the individual evaporation steps of the parent pulp process can be used for the depolymerization.

The lignin-enriched fraction used for the depolarization in step c) preferably has a proportion of compounds which are liquid under standard conditions (20° C. and 1.01325 bar) of at least 10% by weight, particularly preferably at least 20% by weight, in particular at least 30% by weight.

The depolymerization of the lignin-enriched fraction in step c) preferably comprises the following sub-steps:
c1) heating,
c2) depolymerization at elevated temperature,
c3) cooling,
c4) optionally, adjustment of the pH.

In step c1) the lignin-enriched fraction is preferably heated to a temperature in the range from 150 to 350° C., particularly preferably from 200 to 300° C. The critical point is preferably not exceeded during heating in step c1) and in the subsequent depolymerization in step c2), i.e. the reaction mixture is preferably not in a supercritical state during heating and depolymerization.

The heating in step c1) is preferably carried out using heat which originates from the cooling step c3) or another process step of the integrated process for pulp production. For this purpose, the lignin-enriched fraction is preferably passed through a heat exchanger in step c1). If desired, the lignin-enriched fraction can be subjected to additional heating by means of a further heat source. This can be effected by means of a suitable facility on the reactor used for the depolymerization in step c2), by means of which the reaction mixture can also be maintained at the depolymerization temperature.

The depolymerization in step c2) is carried out in a reactor suitable for this purpose, e.g. in a pressure vessel which can additionally have a stirrer and a facility for heating/cooling the contents of the reactor.

The pressure in the depolymerization in step c2) is generally in the range from 1 bar to 300 bar, preferably 2 bar to 100 bar.

The duration of the depolymerization in step c2) is generally from 1 minute to 7 days, preferably 5 minutes to 5 hours.

At least one compound can be added to the lignin-enriched fraction in order to promote the depolymerization and/or control the composition of the aromatics composition obtained in the process of the invention. Suitable compounds are in principle the acids, bases and salts, mentioned under step a) as components of the treatment medium, which are incorporated by reference at this point.

If a lignin-enriched fraction in an alkaline treatment medium is used for the depolymerization, it is possible, in a first embodiment, to dispense with the addition of further compounds. This applies especially when a black liquor from sulfate digestion (Kraft digestion) is used for the depolymerization in step c). In a second embodiment a lignin-enriched fraction in an alkaline treatment medium to which at least one further compound has additionally been added is used for the depolymerization. Preference is given to adding at least one compound selected from among bases, ammonium sulfides, alkali metal sulfides or alkaline earth metal sulfides, alkali metal hydrogensulfides and mixtures thereof to the lignin-enriched fraction.

The addition of at least one compound to promote the depolymerization and/or to control the composition of the aromatics composition obtained in the process of the invention can be carried out before step c1), during the course of step c1), before step c2) or during the course of step c2). Gradual addition before or during the course of one or both steps is likewise possible.

As an alternative to or in addition to the addition of at least one compound in order to promote the depolymerization and/or control the composition of the aromatics composition obtained in the process of the invention, the depolymerization in step c2) can be carried out in the presence of a depolymerization catalyst different from these compounds, e.g. inorganic sulfides (sodium sulfide, tungsten sulfide, copper sulfide, iron sulfide, etc.).

The composition of the aromatics composition obtained can be controlled via the conditions of depolymerization, especially depolymerization temperature, depolymerization time and the compounds comprised in or added to the lignin-enriched fraction. Thus, for example, dealkylation occurs to a significantly lesser degree in the absence of sulfur-comprising compounds than in the presence of sulfur-comprising compounds. Thus, for example, a main product in a depolymerization at a temperature in the range from 250 to 300° C. in the presence of NaOH is guaiacol. If the NaOH is partly, e.g. to an extent of from 10 to 80% by weight, replaced by $Na_2S$ under the same conditions, catechol is obtained as main product and correspondingly less guaiacol is formed. Such relationships have been described by I. T. Clark and J. Green in Tappi, Vol. 51, No. 1, January 1968, pp. 44-48, which is hereby incorporated by reference.

The depolymerization mixture obtained in step c2) is cooled in step c3) to a temperature which is preferably in the range from about 10 to 100° C., particularly preferably from 15 to 60° C.

If the depolymerization mixture obtained in step c2) has a pour point (i.e. a temperature at which the viscous liquid ceases to flow) the depolymerization mixture is preferably cooled in step c3) to a temperature which is at least 0.1° C. above, particularly preferably at least 1° C. above, the pour point.

The heat obtained in step c3) is preferably at least partly reused in the integrated process for producing pulp and an aromatics composition, e.g. in step c1), as described above.

If desired, the pH of the cooled depolymerization mixture obtained in step c3) can be adjusted by addition of at least one acid or at least one base (=step c4). Suitable acids and bases are those mentioned under step a), which is incorporated by reference at this point.

If a lignin-enriched fraction from the digestion of a lignocellulose-comprising starting material with an alkaline treatment medium is used for the depolymerization in step c), the pH is preferably set to a value of not more than 10 in step c4). This applies especially when a black liquor from sulfate digestion (Kraft digestion) is used for the depolymerization in step c). The aromatic alcohols obtained in the depolymerization are thus present in protonated form and can easily be separated off subsequently by extraction. A preferred acid for neutralization is $CO_2$.

Step d)

The isolation of at least one material of value from the treatment product(s) obtained in step c) can be carried out by customary methods known to those skilled in the art, including, for example, filtration, centrifugation, extraction, precipitation, crystallization, distillation or a combination. In this regard, the processes described in step b) for the isolation of the cellulose-enriched fraction and the cellulose-depleted fraction(s) is fully incorporated by reference at this point.

In a specific embodiment of the process of the invention, the isolation of an aromatics composition from a depolymerization product obtained in step c) from a lignin-enriched fraction is carried out in step d).

The isolation of an aromatics composition from the depolymerization product obtained in step c) is preferably effected by extraction. Here, at least part of the aromatics obtained in the depolymerization in step c) is separated off while the residue which remains (organic components and inorganic process chemicals) can be passed to a further work-up and/or thermal utilization preferably in the integrated process for pulp production.

The extraction can be carried out using a solvent (extractant) in which the aromatics obtained in the depolymerization are sufficiently soluble and which is otherwise at least partially immiscible with the depolymerization product. The extractant is then brought into intimate contact with the depolymerization product obtained in step c) and a phase separation is subsequently carried out. The extraction can be carried out in one or more stages.

Suitable extractants are nonpolar solvents, aprotic polar solvents, alcohols and mixtures thereof. These include, for example, aromatic hydrocarbons, such as benzene, toluene, ethylbenzene or xylenes; aliphatic and cycloaliphatic hydrocarbons, such as pentane, hexane, heptane, octane, ligroin, petroleum ether, cyclohexane or decalin; halogenated solvents, such as dichloromethane, chloroform, carbon tetrachloride, dichloroethane or chlorobenzene, alkanols and cycloalkanols, e.g. 1-butanol, 1-pentanol, 1-hexanol, 1-heptanol, 1-octanol, cyclohexane and mixtures of the abovementioned solvents.

The extraction can be carried out discontinuously or continuously. A plurality of discontinuous separation operations can be carried out in succession in a cascade-like fashion, with the residue separated off from the extractant phase in each case being brought into contact with a fresh portion of extractant and/or the extractant being conveyed in countercurrent. For discontinuous operation, the depolymerization product and the extractant are brought into contact with mechanical agitation, e.g. by stirring, in a suitable vessel, the mixture is allowed to rest so as to allow phase separation to occur and one of the phases is removed, advantageously by taking off the denser phase at the bottom of the vessel. To carry out the extraction continuously, the extractant and the depolymerization product are fed continuously to suitable apparatuses in a manner analogous to the discontinuous variant.

The extraction is carried out for example, in at least one mixer-settler combination or at least one extraction column. Suitable mixers include both dynamic and static mixers.

In a preferred embodiment, the isolation of the aromatics composition in step d) comprises the following sub-steps:

d1) extraction of the depolymerization product obtained in step c) to give an aromatics-enriched extract Aan) and an aromatics-depleted residue Aab), d2) separation of the extract Aan) into a fraction Ex) comprising the extractant, a fraction $A_{mono}$) enriched in monomeric aromatics and a fraction $A_{oligo}$) enriched in oligomeric aromatics, d3) recirculation of the fraction Ex) to step d1), d4) optionally, recirculation of at least part of the fraction $A_{oligo}$) to step c).

If desired, the pH of the depolymerization product obtained in step c) can be adjusted by addition of at least one acid or at least one base before the extraction. Furthermore, in the case of a multi-stage extraction, the pH of the depolymerization product used in the first stage and the pH of the residue separated off from the extractant phase in the respective stage can be adjusted by addition of at least one acid or at least one base. Suitable acids are, for example, $CO_2$, $H_2S$ and mineral acids such as hydrochloric acid, sulfuric acid and phosphoric acid. Suitable bases are, for example, alkali metal bases such as sodium hydroxide or potassium hydroxide, alkali metal carbonates such as sodium carbonate or potassium carbonate, alkali metal hydrogencarbonates such as sodium hydrogencarbonate or potassium hydrogencarbonate and alkaline earth metal bases such as calcium hydroxide, calcium oxide, magnesium hydroxide or magnesium carbonate and also ammonia or amines.

In one embodiment of the invention, an alkaline depolymerization product which has a pH in the range from 8 to 14 is used for the extraction in step d). Before the extraction, the pH of the depolymerization product is preferably adjusted to from 1 to 9, preferably from 6 to 8.

For the purposes of the invention, monomeric aromatics are aromatics which have one aromatic ring. Oligomeric aromatics are aromatics which have 2, 3, 4, 5 or up to 10 aromatic rings.

As regards the extraction in step d1), what has been said in general terms above about extraction is incorporated by reference at this point.

The separation of the extract Aan) in step d2) is preferably carried out by distillation.

The separation by distillation of the extract Aan) can be carried out by customary methods known to those skilled in the art. Suitable apparatuses for the separation by distillation comprise distillation columns such as tray columns which can be provided with bubble caps, sieve plates, sieve trays, packings, internals, valves, side offtakes, etc. Especially suitable columns are dividing wall columns which can be provided with side offtakes, recirculations, etc. Distillation can be carried out using a combination of two or more than two distillation columns. Further suitable apparatuses are evaporators such as thin film evaporators, falling film evaporators, Sambay evaporators, etc., and combinations thereof.

The distillation is preferably carried out at a temperature at the bottom in the range from about 30 to 250° C., particularly preferably 50 to 200° C.

The distillation can be carried out under atmospheric pressure or reduced pressure. The pressure in the distillation is preferably in the range from about 0.0005 bar to 1.1 bar, particularly preferably from 0.001 bar to 1.0 bar.

The distillation is preferably carried out in two stages. In the first stage, the fraction $A_{oligo}$) enriched in oligomeric aromatics can be isolated as bottom product and the extractant and the monomeric aromatics can be isolated as overhead product. The overhead product of the first stage can then be separated in a second stage into a fraction Ex) comprising the extractant and a fraction $A_{mono}$) enriched in monomeric aromatics.

The above-described separation of the extract Aan) and its recirculation to step d3) generally enables at least 80% by weight, particularly preferably at least 90% by weight, in particular at least 95% by weight of the extractant to be recovered.

To obtain the maximum yield of monomeric aromatics, at least part of the fraction $A_{oligo}$) and preferably the entire fraction $A_{oligo}$) can be recirculated in step d4) to the depolymerization step c). As an alternative, it is possible to use part or all of the fraction $A_{oligo}$) for production of pulp within the integrated process. Here, it can, for example, be burnt together with the concentrated aromatics-depleted residue Aab) and used for generation of heat.

The aromatics composition isolated in step d) preferably comprises, based on the total weight the aromatics composition, not more than 5% by weight, particularly preferably not more than 1% by weight, of paraffins.

The aromatics composition isolated in step d) preferably comprises, based on the total weight of the aromatics composition, not more than 5% by weight, particularly preferably not more than 1% by weight, of saturated cyclic hydrocarbon compounds.

The aromatics composition isolated in step d) preferably comprises, based on the total weight of the aromatics composition, at least 80% by weight, particularly preferably at least 90% by weight, in particular at least 95% by weight, of monomeric aromatics.

The aromatics composition isolated in step d) comprises aromatics selected, for example from among phenolic compounds, such as monoalkylated, dialkylated and polyalkylated phenols; alkoxyphenols, such as methoxyphenols; dihydroxybenzenes; polyalkylated benzenes; dimeric, trimeric and more highly condensed nonphenolic aromatic compounds, etc. The aromatics composition isolated in step d) comprises, for example, phenol, p-cresol, guaiacol (2-methoxyphenol, 2-hydroxyanisol), catechol (1,2-dihydroxybenzene, pyrocatechol), methylguaiacols, ethylguaiacols, methylcatechols and ethylcatechols as aromatics.

Step e)

The aromatics composition isolated in step d) can optionally be subjected to a separation and/or at least one subsequent reaction (=step e).

The separation of the aromatics composition can be effected, for example, by extraction, distillation or a combination thereof. A specific embodiment is extraction with supercritical solvents, e.g. with supercritical $CO_2$. It is in principle possible to use known processes for distillation, rectification and extraction.

An important flavor is, for example, vanillin (3-methoxy-4-hydroxybenzaldehyde). If the process of the invention for producing an aromatics composition is integrated into a sulfite process for the production of pulp, the aromatics composition isolated from the oxidized sulfite waste liquors comprises vanillin as one component. A process for extracting vanillin from oxidized sulfite waste liquors by means of $CO_2$ is described in WO87/001695. If the process of the invention for producing an aromatics composition is integrated into a sulfate (Kraft) process for the production of pulp, the aromatics composition isolated from the black liquor generally comprises no vanillin or in only small amounts thereof, but generally comprises relatively large amounts of guaiacol, which can be oxidized to vanillin by known methods.

In a specific embodiment, the aromatics composition isolated in step d) is subjected to a dealkylation. Processes for dealkylating aromatics are known to those skilled in the art and comprise, for example, hydrodealkylation or the steam dealkylation.

In a further specific embodiment, the aromatics composition isolated in step d) is subjected to a dehydroxylation. Suitable processes for the reduction of phenols and phenol ethers (hydro-de-hydroxylation, dehydroxylation) are described, for example, in J. March, Advanced Organic Chemistry, 4th edition, Verlag John Wiley & Sons, pp. 442-443 and the references cited therein, which is hereby incorporated by reference.

In a specific embodiment, the aromatics composition isolated in step d) is subjected to a dealkylation and subsequent ring hydrogenation. This gives cyclohexanols, cyclohexanediols and cyclohexanepolyols which can optionally be fractionated by distillation. Furthermore, the cyclohexanols, cyclohexanediols and cyclohexanepolyols can, optionally after prior fractionation, be subjected to oxidation (dehydrogenation) to the corresponding cyclohexanones. The oxidation (dehydrogenation) is, for example, described in J. March, Advanced Organic Chemistry, 4th edition, Verlag John Wiley & Sons, pp. 1167-1171, and the references cited therein, which are hereby incorporated by reference.

Step f)

In step d) an aromatics-depleted residue Aab) can be isolated, in addition to the aromatics composition, from the depolymerization product obtained in step c) and be subjected to further processing (=step f). This further processing is preferably carried out as part of the process for producing pulp, into which the production of the aromatics composition is integrated according to the invention. The further processing is the preferably complete recovery of the process chemicals and the preferably complete thermal utilization of the unusable organic constituents of the residue Aab) obtained in the digestion of the lignocellulose material.

The further processing of the residue Aab) in step f) preferably comprises the following sub-steps:
f1) concentration of the residue Aab),
f2) combustion of the concentrated residue,
f3) recovery of chemicals from the product of combustion.

The above-described further processing of the residue Aab) in step f) is in principle independent of whether the production of the pulp is carried out by sulfite digestion, sulfate digestion or soda digestion or one of the above-mentioned variants of these processes. However, there are significant detailed differences in the recovery of chemicals. This is known in principle by those skilled in the art for all processes for the production of pulp. In the following, the further processing of the residue Aab) will be illustrated by the example of a preferred alkaline digestion process and especially a sulfate (Kraft) digestion.

Concentration of the residue Aab) in step f) can be effected by single-stage or multistage evaporation. Preference is given to a multistage evaporation in 2, 3, 4, 5 or more than 5 evaporation stages. Suitable evaporators are those mentioned above for step c). Preference is given for example, to the use of falling film evaporators, which can be configured, for example, as vertical tube evaporators or horizontal tube evaporators. In vertical tube evaporators, the liquid to be evaporated flows along the inside of the tubes in the types which are predominantly used. As heating medium, it is possible to use condensed heating steam, e.g. from the combustion f2). In vertical tube evaporators, the tube length is typically in the range from 3 and 20 m. Typical internal diameters of the tubes are in the range from 10 mm and 100 mm. Horizontal tube evaporators display a lower pressure drop than vertical tube evaporators. Higher heat transfer coefficients compared to vertical tube evaporation are obtained as a result of jet or droplet impingement from tube to tube. It is also possible to accommodate a larger heat-transfer area based on the volume of the apparatus.

If a plurality of evaporators is used in step f1) these are preferably connected so that optimal heat recovery is made possible (e.g. vapor compression, multieffect evaporation).

The solids content of the concentrated residue Aab) is preferably at least 40% by weight, particularly preferably at least 50% by weight, in particular at least 60% by weight.

The combustion of the concentrated residue in step f2) is carried out in a combustion plant customary for this purpose. This is generally provided with a heat exchanger in order to reuse the heat liberated during combustion in another part of the process of the invention or in another process. For this purpose, heat is, for example, taken from the flue gases formed during combustion and used for steam generation. The flue gases are subjected to further purification, e.g. to remove mercaptans comprised. Part of the energy obtained in this way can be used in the process of the invention, e.g. in the evaporation step f1. The excess energy can be used in another way, for example in the likewise very energy-intensive production of paper which is generally associated with the production of pulp. If direct heat coupling, e.g. with a paper factory is not possible, the excess heat can be moved for power generation.

In a specific embodiment of step f2) the concentrated residue Aab) is fed into the combustion space of a combustion plant. Here, the residue is preferably finely dispersed, e.g. by spraying. Residual liquid evaporates and the solids of the residue are pyrolysed. The combustion is generally carried out under reducing conditions. In the sulfate process, sodium sulfate is added to the combustion (as make-up chemical), and this is reduced to sodium sulfide. At the same time, sodium hydroxide is converted into sodium carbonate. The solid residue from the combustion is dissolved in water and used as green liquor for the recovery of chemicals in step f3).

In step f3) in the case of the sulfate process, the green liquor is subjected to causticizing to convert sodium carbonate into sodium hydroxide. The resulting white liquor is then reused for the digestion in step a). Causticization can be integrated into a lime burning process. Here, calcium oxide (quicklime) is produced from calcium carbonate (as further make-up chemical) by calcination, this is quenched to give calcium hydroxide (slaked lime) and the causticization is carried out using the latter, resulting in reformation of calcium carbonate which can then once again be used for the burning of lime.

The above-described process is shown quite generally schematically in FIG. 1.

Figure 2:
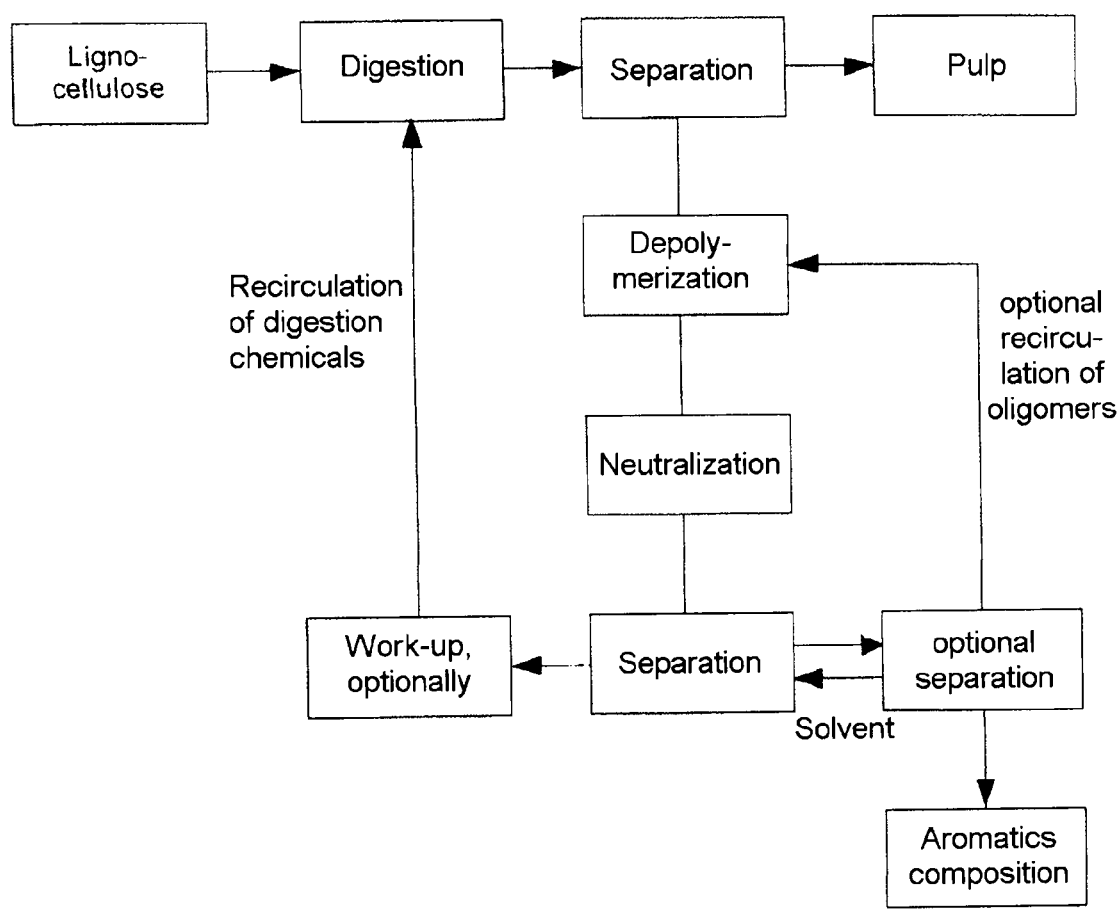

FIG. 2 shows an integrated process for producing pulp and an aromatics composition, wherein
a) a lignocellulose-comprising starting material is provided and subjected to digestion with a treatment medium,
b) a cellulose-enriched fraction and a lignin-enriched fraction are isolated from the digested material, with the lignin-enriched fraction comprising at least part of the treatment medium from step a),
c) the lignin-enriched fraction is subjected to depolymerization and d) an aromatics composition is isolated from the depolymerization product obtained in step c).

A specific embodiment is an integrated process for producing pulp and an aromatics composition, wherein
a) a lignocellulose-comprising starting material is provided and subjected to digestion with a treatment medium,
b) a cellulose-enriched fraction and a lignin-enriched fraction are isolated from the digested material, with the lignin-enriched fraction comprising at least part of the treatment medium from step a),
c) the lignin-enriched fraction is subjected to depolymerization and
d) an aromatics composition is isolated by extraction from the depolymerization product obtained in step c),
e) the aromatics composition isolated in step d) is optionally subjected to a fractionation and/or at least one subsequent reaction,
f) an aromatics-depleted residue is isolated in step d) from the depolymerization product and subjected to further processing to give at least one component which is comprised in the treatment medium used in step a), and
g) the component(s) of the treatment medium obtained in step f) is/are recirculated to step a).

Figure 3:
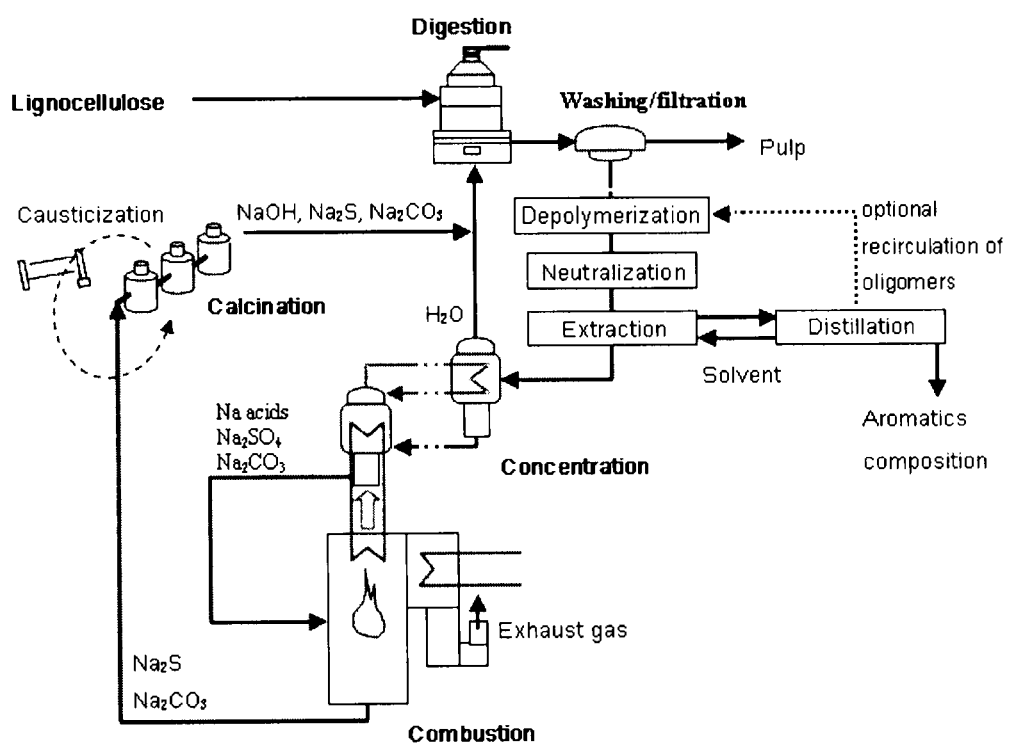

FIG. 3 shows an embodiment of the process of FIG. 2, in which the production of aromatics is integrated into a sulfate (Kraft) process.

The invention is illustrated by the following, nonlimiting examples.

EXAMPLES

I) Thermal treatment

Example 1

Cracking of Black Liquor at 290° C. in an Autoclave 100 g of black liquor (from StoraEnso, lignin content about 5%) were heated at 290° C. in a 0.3 l HD autoclave material HC for 1 hour while stirring. After cooling, the reaction product mixture was diluted with 70 ml of water, set to a pH of 2 by means of hydrochloric acid (37%) and filtered. The filter cake was extracted with diisopropyl ether in a Soxhlett apparatus and the aqueous phase was extracted with diisopropyl ether in a separating funnel. The combined organic phases were dried over magnesium sulfate and the solvent was removed by distillation. This gave 2.2 g (44%) of residue and 2.4 g (48%) of extract. The extract was analyzed by GC in THF using heptadecane as internal standard. The aromatics phenol (0.25% by weight), guaiacol (1.8% by weight), pyrocatechol (4.4% by weight) and vanillin (0.6% by weight) were determined quantitatively.

Example 2

Cracking of Black Liquor at 240° C. in an Autoclave 100 g of black liquor (from StoraEnso, lignin content about 5%) were heated at 240° C. in a 0.3 l HD autoclave material HC for 1 hour while stirring. After cooling, the reaction product mixture was diluted with 70 ml of water, set to a pH of 2 by means of hydrochloric acid (37%) and filtered. The filter cake was extracted with diisopropyl ether in a Soxhlett apparatus and the aqueous phase was extracted with diisopropyl ether in a separating funnel. The combined organic phases were dried over magnesium sulfate and the solvent was removed by distillation. This gave 4.2 g (84%) of residue and 0.7 g (14%) of extract. The extract was analyzed by GC in THF using heptadecane as internal standard. The aromatics phenol (0.07% by weight), guaiacol (0.76% by weight), pyrocatechol (1.1% by weight) were determined quantitatively.

Example 3

Comparison with the Cracking of Dissolved Kraft Lignin at 290° C. in an Autoclave 5 g of Kraft lignin (from Lignoboost AB) dissolved in 5% sodium hydroxide solution (80 g) were heated at 290° C. in a 0.3 l HD Autoklav Material HC for 1 hour while stirring. After cooling, the reaction product mixture was diluted with 70 ml of water, set to a pH of 2 by means of hydrochloric acid (37%) and filtered. The filter cake was extracted with diisopropyl ether in a Soxhlett apparatus and the aqueous phase was extracted with diisopropyl ether in a separating funnel. The combined organic phases were dried over magnesium sulfate and the solvent was removed by distillation. This gave 2.2 g (44%) of residue and 1.2 g (22%) of extract. The extract was analyzed by GC in THF using heptadecane as internal standard. The aromatics phenol (0.6% by weight), guaiacol (0.4% by weight), pyrocatechol (23.8% by weight) and vanillin (0.44% by weight) were determined quantitatively.

Example 4

Cracking at 290° C. in a Continuous Reactor

16% by weight of Kraft lignin (from Lignoboost AB) were dissolved in 2 N sodium hydroxide solution and passed continuously through a reactor tube at 290° C. and a residence time of 10 minutes in the reactor. The reaction product mixture was set to a pH of 2 by means of hydrochloric acid (37%) and filtered. The filter cake was extracted with diisopropyl ether in a Soxhlett apparatus and the aqueous phase was extracted with diisopropyl ether in a separating funnel. The combined organic phases were dried over magnesium sulfate and the solvent was removed by distillation. A 100 ml sample of the reaction product mixture gave 10.3 g (64.4%) of residue and 3.2 g (20%) of extract. The extract was analyzed by GC in THF using heptadecane as internal standard. The aromatics guaiacol (6.1% by weight) and pyrocatechol (4.7% by weight) were determined quantitatively.

II) Comparative Examples: Extraction of an Untreated Black Liquor

Example 5

447 g of an untreated black liquor having a pH of 12.5 were set to a pH of 7.0 by means of $CO_2$. 447 g of 1-hexanol were subsequently added as extractant and the mixture was stirred vigorously at room temperature for 10 minutes. The phases were then separated under gravity. After settling, 472 g of organic phase and 422 g of aqueous phase were obtained. The organic phase was evaporated to leave 1.8 g of evaporation residue. The vapor was condensed and analyzed by means of gas chromatography (GC). 1.2% by area of an aromatics-rich fraction were found therein. Under the assumption that the proportions by weight correspond to the proportions by area, 5.7 g of aromatics-rich fraction were able to be obtained from the untreated black liquor.

III) Examples Using a Black Liquor Treated According to the Invention

Example 6

Untreated black liquor was thermally treated according to the invention at 290° C. for 1 minute. 447 g of this black liquor which had been treated according to the invention (i.e. the same amount as in example 5) were set to a pH of 7.7 by means of $CO_2$. 447 g of 1-hexanol were then again added as extractant and the mixture was stirred vigorously at room temperature for 10 minutes. The phases were then separated in a centrifuge. After settling, 389 g of organic phase and 186 g of aqueous phase were obtained. After the phase separation, a third phase (about 164 g) was present between the organic phase and the aqueous phase. In addition, a pure solid phase (about 155 g) was formed. The clear organic phase was evaporated to leave 5.8 g of evaporation residue. The vapor was condensed and analyzed by means of GC. 14.7% by area of an aromatics-rich fraction were found therein. Under the assumption that the proportions by weight correspond to the proportions by area, 57.2 g of aromatics-rich fraction were able to be obtained from the black liquor which had been treated according to the invention.

CONCLUSION

Compared to the untreated black liquor, a 10-fold greater amount (=57.2 g/5.7 g) of an aromatics-rich fraction could be obtained from the black liquor which had been treated by the process of the invention after neutralization with $CO_2$. Any aromatics from the third phase and the solid phase are not taken into account.

The invention claimed is:

1. An integrated process for producing pulp and at least one low molecular weight material of value, the process comprising:
    a) digesting a lignocellulose-comprising starting material with a treatment medium;
    b) isolating a cellulose-enriched fraction and at least one cellulose-depleted fraction from the digested material, with the at least one cellulose-depleted fraction comprising at least part of the treatment medium from the digesting a);
    c) depolymerizing the at least one cellulose-depleted fraction, to give a treatment product comprising the at least one low molecular weight material of value; and
    e) isolating the at least one material of value from the treatment product obtained in c).

2. The process according to claim 1, wherein the treatment medium in the digesting a) is an alkaline treatment medium.

3. The process according to claim 2, further comprising:
    treating the lignocellulose-comprising starting material with at least one selected from the group consisting of a mineral acid and steam, before the digesting with the alkaline treatment medium.

4. The process according to claim 2, wherein the treatment medium in the digesting a) comprises NaOH and $Na_2S$ in an aqueous medium.

5. The process according to claim 2, wherein the treatment medium in the digesting a) comprises NaOH in an aqueous medium which is essentially free of any sulfur-comprising compounds.

6. The process according to claim 1, wherein the treatment medium in the digesting a) comprises at least one organic solvent.

7. The process according to claim 1, wherein the isolating of the cellulose-enriched fraction and the at least one cellulose-depleted fraction in b) is effected by at least one selected from the group consisting of filtration, centrifugation, extraction, precipitation, distillation, and stripping.

8. The process according to claim 1, wherein the cellulose-enriched fraction isolated in the isolating b) is subjected to a purification to remove any remaining treatment medium from the digesting a).

9. The process according to claim 8, wherein, in the purification, the cellulose-enriched fraction is subjected to washing with a liquid washing medium.

10. The process according to claim 9, wherein the liquid washing medium comprises water.

11. The process according to claim 9, wherein the liquid washing medium, after washing, is at least partly combined with the at least one cellulose-depleted fraction.

12. The process according to claim 9, wherein the liquid washing medium consists of water.

13. The process according to claim 1, wherein a cellulose-depleted fraction comprising at least one component selected from the group consisting of lignin, hemicellulose, cellulose, a degradation product of lignin, a degradation product of hemicellulose, and a degradation product of cellulose, is isolated from digested material in the isolating b).

14. The process according to claim 1, wherein the treating c) is at least one treatment selected from the group consisting of depolymerization, hydrocracking, and decarboxylation.

15. The process according to claim 14, wherein the cellulose-depleted fraction for the treating c) comprises at least one liquid compound in a proportion of at least 10% by weight, based on the total weight, and
    the at least one liquid compound is liquid under standard conditions (20° C. and 1.01325 bar).

16. The process according to claim 14, wherein an alkaline, cellulose-depleted fraction additionally comprising at least one selected from the group consisting of a sulfide and a hydrogensulfide, is subjected in the treating c) to the depolymerization at a temperature in a range from 150 to 250° C.

17. The process according to claim 16, wherein a residence time at the temperature of the depolymerization is from 5 seconds to 5 minutes.

18. The process according to claim 16, wherein part of the at least one liquid compound comprised is removed from the alkaline, cellulose-depleted fraction before the depolymerization in c) and at least part of the at least one liquid compound, comprised in a depolymerization residue obtained after the depolymerization and after the isolating of the at least one material of value is removed from the depolymerization residue.

19. The process according to claim 1, where the at least one material of value is selected from the group consisting of hydrogen, an unfunctionalized aliphatic hydrocarbon, an unfunctionalized cycloaliphatic hydrocarbon, an unfunctionalized aromatic hydrocarbon, a functionalized aliphatic hydrocarbon, a functionalized cycloaliphatic hydrocarbon, and a functionalized aromatic hydrocarbon.

20. The process according to claim 1, where the at least one material of value is selected from the group consisting of hydrogen, an alkane, an alkenes, an alkadienes, an alkanols, an aliphatic aldehydes, a cycloalkanes, a cycloalkenes, a cycloalkadienes, a cycloalkanols, a cycloalkadienols, a cycloalkane polyol having more than 2 OH groups, an aromatic hydrocarbon, an aromatic alcohol, and an aromatic aldehyde.

21. An integrated process for producing pulp and an aromatic composition, the process comprising:

a) digesting a lignocellulose-comprising starting material with a treatment medium, to obtain digested material;

b) isolating a cellulose-enriched fraction and a lignin-enriched fraction from the digested material, with the lignin-enriched fraction comprising at least part of the treatment medium from the digesting a);

c) depolymerizing the lignin-enriched fraction, to obtain a depolymerization product; and d) isolating an aromatics composition from the depolymerization product obtained in the depolymerizing c).

22. The process according to claim 21, wherein the isolating of the cellulose-enriched fraction and the lignin-enriched fraction in b) is effected by filtration or centrifugation.

23. The process according to claim 21, wherein the cellulose-enriched fraction isolated in b) is subjected to a purification to remove any remaining treatment medium from a).

24. The process according to claim 23, wherein the purification is a washing with a liquid washing medium and a loaded washing medium obtained after the washing is at least partly combined with the lignin-enriched fraction.

25. The process according to claim 21, wherein a black liquor, obtained from the digesting of the lignocellulose-comprising starting material with an alkaline treatment medium which is the treatment medium, is employed in the depolymerizing c).

26. The process according to claim 25, wherein a black liquor from sulfate digestion (Kraft digestion) in the digesting a) is employed in the depolymerizing c).

27. The process according to claim 21, wherein part of at least one liquid compound comprised in the lignin-enriched fraction is removed from the lignin-enriched fraction before the depolymerizing c).

28. The process according to claim 21, wherein the lignin-enriched fraction in the depolymerizing c) has a proportion of at least one compound which is liquid under standard conditions (20° C. and 1.01325 bar) of at least 10% by weight.

29. The process according to claim 21, wherein the depolymerizing of the lignin-enriched fraction in c) comprises:
   c1) heating;
   c2) depolymerizing at elevated temperature;
   c3) cooling; and
   c4) optionally, adjusting of the pH.

30. The process according to claim 21, wherein, in the isolating d), an aromatic composition is isolated by extraction from the depolymerization product obtained in c).

31. The process according to claim 21, wherein the isolating of the aromatic composition in d) comprises:
   d1) extracting the depolymerization product obtained in c), to give an aromatics-enriched extract Aan) and an aromatics-depleted residue Aab);

d2) separating the extract Aan) into
      a fraction Ex) comprising an extractant, a fraction $A_{mono}$) enriched in monomeric aromatics, and
      a fraction $A_{oligo}$) enriched in oligomeric aromatics;
   d3) recirculating the fraction Ex) to the extracting d1); and
   d4) optionally, recirculating at least part of the fraction $A_{oligo}$) to the depolymerizing c).

32. The process according to claim 21, further comprising:
   e) subjecting the aromatics composition isolated in d) to at least one selected from the group consisting of a separation and a subsequent reaction.

33. The process according to claim 21, further comprising:
   f) isolating the aromatics-depleted residue Aab) from the depolymerization product in d), to give an isolated aromatics-depleted residue and further processing the isolated aromatics-depleted residue.

34. The process according to claim 33, wherein the further processing of the isolated aromatics-depleted residue in f) comprises:
   f1) concentrating the isolated aromatics-depleted residue, to obtain a concentrated residue;
   f2) combusting the concentrated residue, to give a combustion product; and
   f3) recovering at least one chemical from the combustion product.

35. An integrated process for producing pulp and an aromatics composition, the process comprising:
   a) digesting a lignocellulose-comprising starting material with a treatment medium, to obtain a digested material;
   b) isolating a cellulose-enriched fraction and a lignin-enriched fraction from the digested material, with the lignin-enriched fraction comprising at least part of the treatment medium from a);
   c) depolymerizing the lignin-enriched fraction to obtain a depolymerization product;
   d) isolating an aromatics composition by extraction from the depolymerization product obtained in c),
   e) optionally, subjecting the aromatics composition isolated in d) to at least one selected from the group consisting of a fractionation and a subsequent reaction;
   f) isolating an aromatics-depleted residue in d) from the depolymerization product, to obtain an isolated aromatics-depleted residue, and further processing the isolated aromatics-depleted residue, to give at least one component which is comprised in the treatment medium employed in the digesting a), and
   g) recirculating the component of the treatment medium obtained in f) to the digesting a).

* * * * *